US012690791B2

(12) United States Patent
Viirre et al.

(10) Patent No.: US 12,690,791 B2
(45) Date of Patent: Jul. 28, 2026

(54) QUANTUM COMPUTING FOR MAGNETO-ENCEPHALOGRAPHY

(71) Applicants: Google LLC, Mountain View, CA (US); The Regents of the University of California, Oakland, CA (US)

(72) Inventors: Erik Scott Viirre, San Diego, CA (US); Jarrod Ryan McClean, Underwood, CA (US)

(73) Assignee: Google LLC, Mountain View, CA (US)

( * ) Notice: Subject to any disclaimer, the term of this patent is extended or adjusted under 35 U.S.C. 154(b) by 0 days.

(21) Appl. No.: 18/931,262

(22) Filed: Oct. 30, 2024

(65) Prior Publication Data

US 2026/0114776 A1     Apr. 30, 2026

(51) Int. Cl.
*A61B 5/00*       (2006.01)
*A61B 5/245*      (2021.01)
*G06N 10/40*      (2022.01)

(52) U.S. Cl.
CPC ............ *A61B 5/245* (2021.01); *A61B 5/7203* (2013.01); *G06N 10/40* (2022.01); *A61B 2562/0223* (2013.01); *A61B 2562/046* (2013.01)

(58) Field of Classification Search
CPC .................. A61B 5/245; A61B 5/7203; A61B 2562/0223; A61B 2562/046; G06N 10/40
See application file for complete search history.

(56) References Cited

U.S. PATENT DOCUMENTS

| | | | |
|---|---|---|---|
| 8,618,799 B1 | 12/2013 | Radparvar et al. | |
| 2020/0253479 A1* | 8/2020 | Nurmikko | A61B 5/14553 |
| 2020/0321124 A1* | 10/2020 | Ford | A61B 5/7267 |
| 2022/0156623 A1* | 5/2022 | Escamilla | G06N 3/061 |
| 2023/0206104 A1* | 6/2023 | Rab | G06N 10/00 716/100 |
| 2024/0069634 A1 | 2/2024 | OrÚs et al. | |
| 2024/0100351 A1* | 3/2024 | Phillips | A61B 5/4836 |

FOREIGN PATENT DOCUMENTS

WO        2014055293 A1      4/2014

OTHER PUBLICATIONS

Huang, Hsin-Yuan, et al., "Quantum advantage in learning from experiments", Science376, 1182-1186(2022). DOI:10.1126/science. abn7293, 5 pages.
King, Robbie, et al., "Exponential learning advantages with conjugate states and minimal quantum memory", arXiv:2403.03469v1 [quant-ph] Mar. 6, 2024, pp. 1-46.
International Search Report and Written Opinion for International Application No. PCT/US2025/052013 dated Jan. 8, 2026, 16 Pages.

* cited by examiner

*Primary Examiner* — Alexei Bykhovski
(74) *Attorney, Agent, or Firm* — Botos Churchill IP Law

(57) ABSTRACT

Aspects provide systems and methods for utilizing quantum computing systems for processing of data generated by quantum sensor. For example, magnetic field data may be captured from a brain using a quantum sensor array. This magnetic field data may then be processed using a quantum computing apparatus including a plurality of qubits in order to generate a model of the brain.

20 Claims, 9 Drawing Sheets

910 ─── Capturing magnetic field data from a brain using a quantum sensor array

920 ─── Processing the magnetic field data using a quantum computing apparatus including a plurality of qubits in order to generate a model of the brain

900

100

200

600

800

910

920

900

QUANTUM COMPUTING FOR MAGNETO-ENCEPHALOGRAPHY

BACKGROUND

Localization and measurement of signals in the human brain is a crucial diagnostic and explanatory tool in both clinical and academic settings. For instance, magneto-encephalography tests may detect magnetic fields produced by neuron action in the brain and localize the origin of those fields in both time and space. These may be especially useful in identifying the location of the sources of epileptic seizures in individuals. A key challenge faced by this method is the relative weakness of magnetic field signals that are produced within the brain, which can lead to long collection times, higher than desired signal to noise, and general challenges in mapping single event data. Although magneto-encephalography tests are a powerful tool for measuring brain activity and correlating an action or response to a stimulus with brain activity at high spatiotemporal resolution, the relatively weak signal means that signal collection time must be long, and measurements must focus on averaged repetitions of an action or stimulus. To mitigate these challenges, sophisticated passive shielding methods in combination with very sensitive superconducting quantum interference detectors (SQUIDs) are used, but to date, such detectors have been used in a classical mode of operation with only classical computation. As a result, the data analysis of the collected signals can be prohibitive computationally today.

BRIEF SUMMARY

Aspects of the disclosure provide a method. The method includes capturing magnetic field data from a brain using a quantum sensor array; and processing the magnetic field data using a quantum computing apparatus including a plurality of qubits in order to generate a model of the brain.

In one example, the quantum sensor array includes a plurality of Superconducting Quantum Interference Devices (SQUIDs) configured to measure magnetic field gradients generated by brain activity. In another example, the quantum sensor array is configured as a mesh network linked to the quantum computing apparatus such that the magnetic field data is processed in quantum form. In another example, the quantum sensor array and the quantum computing apparatus are each at least partially housed within a dewar. In another example, the method also includes, prior to processing the magnetic field data using a quantum computing apparatus, processing the magnetic field data using a classical computing device including one or more processors to generate classical data such that the classical data is processed by the quantum computing apparatus. In another example, the model represents physical origin of signal generation within the brain. In another example, the model is a classical electromagnetic field model. In another example, the model is a quantum field model where a coherent photon field models actions and coordination within the brain. In another example, processing the magnetic field data further includes identifying an action, and the method further includes sending a signal to a device in order to cause the device to perform the action. In another example, the method also includes using the processed magnetic field data to set test variables for a quantum computing problem. In another example, the method also includes, in response to processing the magnetic field data, adjusting a characteristic of the quantum sensor array in order to improve signal quality.

Another aspect of the disclosure provides a system. The system includes a quantum sensor array configured to capture magnetic field data from a brain; and a quantum computing apparatus including a plurality of qubits and configured to process the magnetic field data in order to generate a model of the brain.

In one example, the quantum sensor array is configured as a mesh network linked to the quantum computing apparatus such that the magnetic field data is processed in quantum form. In another example, the quantum sensor array and the quantum computing apparatus are each at least partially housed within a dewar. In another example, the system also includes a classical computing device including one or more processors configured to, prior to the quantum computing apparatus processing the magnetic field data, processing the magnetic field data to generate classical data. In another example, the model represents physical origin of signal generation within the brain. In another example, the model is a quantum field model where a coherent photon field models actions and coordination within the brain. In another example, the quantum computing apparatus is further configured to process the magnetic field data to further identifying an action and to send a signal to a device in order to cause the device to perform the action. In another example, the quantum computing apparatus is further configured to use the processed magnetic field data to set test variables for a quantum computing problem. In another example, the quantum computing apparatus is further configured to, in response to processing the magnetic field data, adjust a characteristic of the quantum sensor array in order to improve signal quality.

DETAILED DESCRIPTION

Overview

Figure 1:
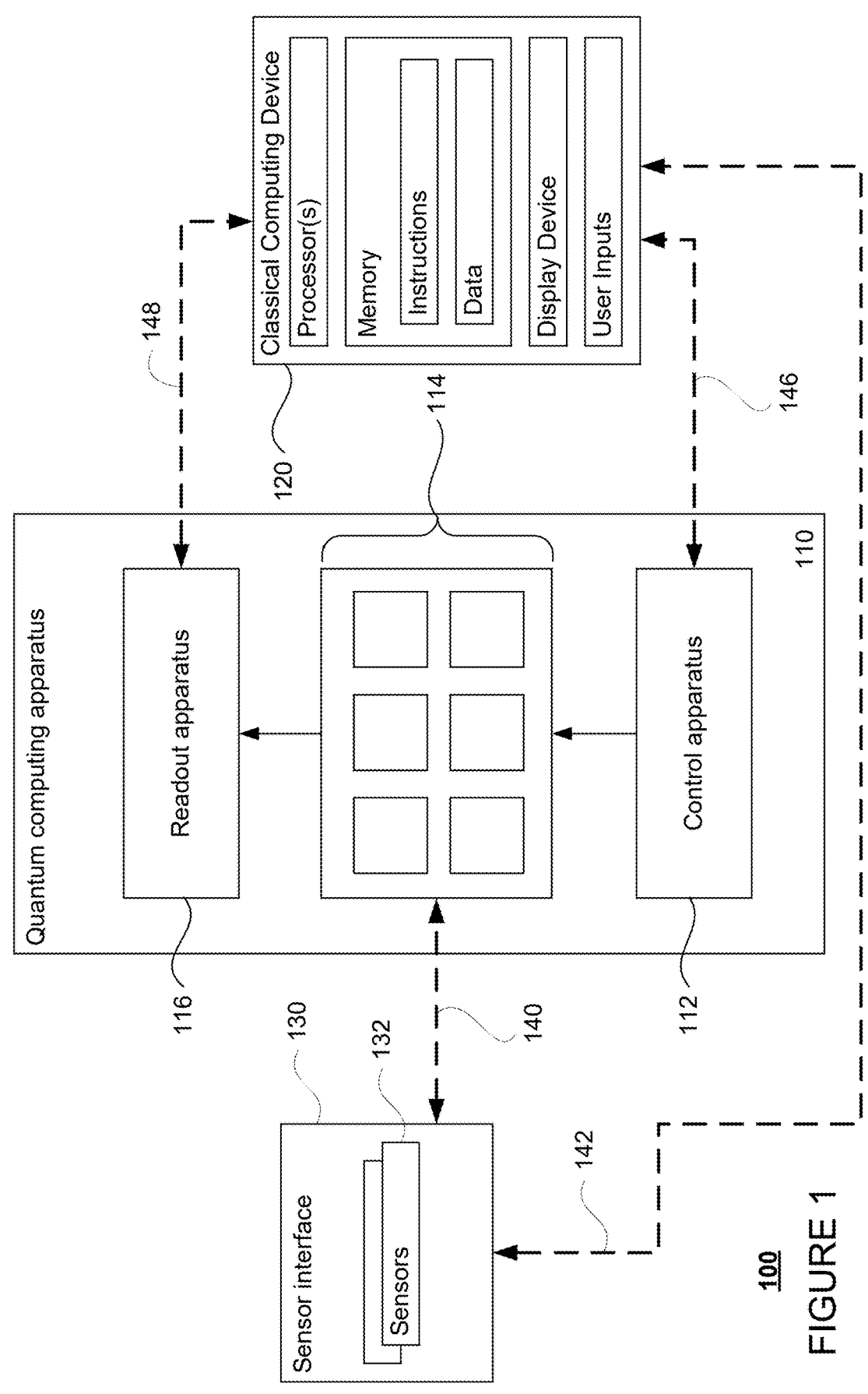
FIG. 1 is an example quantum computing system arrangement in accordance with aspects of the technology.

The technology relates to utilizing quantum computing systems for processing of data generated by quantum sensors. For instance, magneto-encephalography, which utilizes very sensitive superconducting quantum interference detectors (SQUIDs), may enable the identification and analysis of certain facets of the brain of an individual (e.g., a patient). However, the technique is limited in many ways by the relatively weak signals on which it relies, leading to long collection times, poor signal to noise, and limitation to averaged signal collections. Moreover these detectors are typically used in a classical mode of operation and in combination with only classical computation, despite the quantum nature of the detectors. In a classical (non-quantum) computing system, the signals output by the SQUIDs may be collapsed and recorded to memory of the classical computing device. In such instances, the output signals may be minimally processed by control fields before being reduced to classical field and phase values in order to develop a model of the output signals correlated to different actions or stimuli. For example, a classical electromagnetic field model may be used to explain the spatial origin of signals within the brain that may exhibit coherence. However, such an approach may lack essential quantum features that could be detectable with the unique data collection combination discussed herein. To address these deficiencies, data generated by the detectors can be processed using quantum computing systems thereby dramatically improving data processing and analysis.

An example system may include a sensor interface, a quantum computing apparatus and a classical computing device. The sensor interface may include a plurality of sensors having quantum properties arranged as one or more quantum sensor arrays. The individual sensors of a quantum sensor array may be linked in different configurations. In one example, the sensors may be linked internally (sensor to sensor) such that the array is set up as a mesh network which is linked to the quantum computing apparatus or the classical computing device. This link may be a classical link or a quantum link.

The quantum computing apparatus may include one or more physical qubits, which can be used to perform quantum processing for various tasks and operations. Depending upon the architecture of the quantum computing system, various different types of qubits may be used. Depending upon the qubits used, the sensor interface and the quantum computing apparatus may be at least partially and/or fully housed within a super-cooled dewar.

The quantum computing system may be used to collect, process and analyze data generated by the sensors of the sensor interface during a magneto-encephalography test. For example, the one or more quantum sensor arrays may be placed near the brain from which signals are to be collected. In this regard, the sensor interface may include a cap or other device placed on an individual's head. The data collection may begin, during which an action may be performed by the individual or some stimulus, such as visual, tactile or audible, may be provided.

The individual sensors of the one or more quantum sensor arrays may respond to magnetic fields generated by electrical activity in a brain and generate an output signal representing the gradient of the magnetic field or the rate of change of the magnetic field strength.

In some instances the signals generated by sensors may be processed minimally within the sensor array via the quantum links. For instance, the quantum sensor array may encode additional data in the output signals. This additional data may include, for example, sensor location and relative phase and timing information internal to the sensor which can be used by a classical computing system or a quantum computing apparatus to process the magnetic field data.

Because of the quantum nature of the one or more quantum sensor arrays, the output signals may be directly transduced from the sensors to the quantum computing apparatus. In this configuration, a resonator may be used as both a field controller for a given qubit as well as an output reader of the qubit's processing of the variables posed to an entangled qubit pair. The output signals may be encoded in a quantum error correcting code, in order to enable further use of the out signals. Because of the direct connection between the one or more quantum sensor arrays, processing can therefore be made in an extremely low noise environment, thereby increasing the signal to noise quality. For example, integrating the quantum system inside of super-cooled dewar may ensure a stable and optimal operating environment for the SQUIDs and the quantum computing apparatus, reducing the risk of errors due to quantum decoherence and other noise sources. The noise reduction may enable faster tests with more reliable results.

Alternatively, the output signals may be processed by the classical computing device or the quantum computing apparatus in order to reduce the output signals to classical field and phase values. These may be stored in classical or quantum memory depending upon the configuration of the system.

The quantum computing apparatus may then be used to process the output signals (quantum data) or the classical data. The quantum data may be processed directly with quantum learning algorithms to determine various features of the output signals. In some instances, quantum error correction encodings may be used to preserve and/or purify the output signals as required for processing. This may enable quantum learning algorithms to extract novel signals with exponentially fewer samples in some cases. In this regard, the output signals may be processed in their quantum form rather than after such signals are converted to classical form which may provide significant potential advantages for learning about the individual's brain activity or such activity in general.

For the classical data, the encoded data may be used by the quantum computing system with quantum signal processing techniques to extract signals from the data. In this regard, the quantum data or classical data may be run through classical data processing techniques via the quantum computing system or a classical computing device.

The quantum computing apparatus may then be used to generate various models. For example, the quantum computing apparatus may generate a model of the physical origin of signal generation within the brain that is fundamentally quantum in nature in that it supports coherence, contextuality, and entanglement. This model may be fit to the various features to better explain the origin of signals within the brain that are collected and analyzed.

As another example, the quantum computing apparatus may generate a model of the underlying signal-action relationship within the individual's brain. This model may be a classical electromagnetic field model (e.g. dipole source) to localize events in space and time using analytic procedures such as an inverse "best fit" describing the signal origin or a novel quantum field model where a coherent photon field models the actions and coordination within the individual's brain.

The models may be used to deliver feedback to the individual in real time (e.g., during the magneto-encephalography test). This feedback may be in the form of additional external stimulus either classical or quantum. In some instances, the entire procedure may be looped to enable control of another device by the individual as discussed further below.

The features described herein may provide a significant improvement over existing technologies, by offering a more sophisticated and powerful tool for data processing and analysis. The features described herein bring the immediate computation power of quantum computing to the problems of clinical and basic neuroscience. In some instances, the output data generated and processed as described herein may reveal different underlying brain activity than classical analysis which may potentially lead to significant advancements in the ability to understand and interact with the brain as well as enable detection of novel phenomena and mechanisms enabled by primarily quantum pathways. This unique combination opens up new possibilities in the fields of quantum sensing and detection, neuroimaging, brain research, diagnostics and diagnosis of diseases of the brain, surgical planning, brain-computer interface systems and more.

Example Systems

FIG. 1 provides a simplified overview of an example quantum computing system 100. The system comprises a quantum computing apparatus 110, a classical computing device 120, and a sensor interface 130 each connected via links 140, 142, 146, 148. Such links (including link 144 of FIGS. 3 and 5) may represent wired or wireless connections. The quantum computing apparatus 110 comprises one or more physical qubits 114, which can be used to perform quantum processing for various tasks and operations. In the example shown, six qubits 114 are present, although more or fewer qubits can be used. Each qubit 114 is a physical system with three or more quantum levels. Two of the quantum levels are taken to form the computational subspace, e.g., the states $|0\rangle$ and $|1\rangle$. These may, in some implementations, be the lowest two energy states of the physical system being used as a qubit. The remaining one or more states form the non-computational (or leakage) subspace, e.g., $|2\rangle$, $|3\rangle$ etc.

The quantum computing apparatus may include one or more physical qubits, which can be used to perform quantum processing for various tasks and operations. Depending upon the architecture of the quantum computing system, various different types of qubits may be used. For instance, the qubits 114 may be microwave superconducting qubits that can be responsive to applied microwave signals. In this example, the qubits may be transmon-type qubits, spin qubits, or quantum dots. Alternatively, the qubits may be of other types, such as gmon, fluxmon, fluxonium, capacitively-shunted flux, photonic qubits, Rydberg qubits, trapped ions, etc.

The quantum computer further comprises a control apparatus 112. The control apparatus 112 may be configured to apply control signals to one or more the qubits 114 in order to alter a state or property of the qubits. For example, the control apparatus 112 can apply control signals to the qubits 114 in order to implement one or more quantum gates on the qubits 114. The control apparatus 112 may include a set of one or more control lines for transmitting control signals to the one or more qubits 114. The control signals may, for example, comprise control pulses for altering states on the one or more qubits 114. Such control pulses may be, e.g., in the form of microwave control pulses. An example of such a microwave control pulse is a 7-pulse, which acts to exchange the populations (e.g., the amplitudes) of quantum states in the one or more qubits 114.

As shown, the quantum computer further includes a readout apparatus 116 which may include one or more resonator arrays (resonators). The readout apparatus 116 is configured to perform measurements on the one or more qubits 114. Performing measurements involves sending a signal into the system and receiving a signal out of the system, where the received signal is shifted in phase or amplitude based on the qubit state. Thus, based on the results of the measurements, the readout apparatus 116 provides output indicative of the state of the one or more qubits 114. For example, the readout apparatus 116 may provide an output of "0" or "1" corresponding to the $|0\rangle$ and $|1\rangle$ states of the qubit respectively for each of the qubits in the assembly. As another example, the readout apparatus 116 may provide an output of "00", "01", "10", or "11" corresponding to the 2-qubit $|00\rangle$, $|01\rangle$, $|10\rangle$ and $|11\rangle$ states of each qubit respectively. As shown, the readout apparatus 116 is a separate component to the control apparatus 112. However, in other implementations the readout apparatus 116 may be a part of the control apparatus 112.

The classical computing device 120 may interact with the control apparatus 112 to control operation of the classical computing device 120, such as via link 146. For example, a user interface for the control apparatus 112 (not shown) may be provided through the classical computing device 120. The classical computing device 120 may also process measurement data/readout states from the readout apparatus 116, such as via link 148, to determine properties of the qubits 114, such as the average population of quantum states. For example, a user 122 (depicted in FIG. 2) may interact with the classical computing device 120 in order to control and/or access information from the quantum computing apparatus 110.

As shown, the classical computing device 120 includes one or more processors and memory that is configured to store instructions and data. The processors may be any conventional non-quantum computing processors, such as commercially available CPUs, TPUs, graphical processing units (GPUs), etc. Alternatively, each processor may be a dedicated device such as an ASIC or other hardware-based processor. The memory may be of any type capable of storing information accessible by the processor(s), including a computing device-readable medium. The memory is a non-transitory medium such as a hard-drive, memory card, optical disk, solid-state, etc.

Although FIG. 1 functionally illustrates the processor(s) and memory as being within the same block, such devices may actually include multiple processors, computing devices, or memories that may or may not be stored within the same physical housing. Similarly, the memory may be a hard drive or other storage media located in a housing different from that of the processor(s), for instance in a cloud computing system. Accordingly, references to a processor or computing device of the classical computing device will be understood to include references to a collection of processors or computing devices or memories that may or may not operate in parallel.

Figure 4:
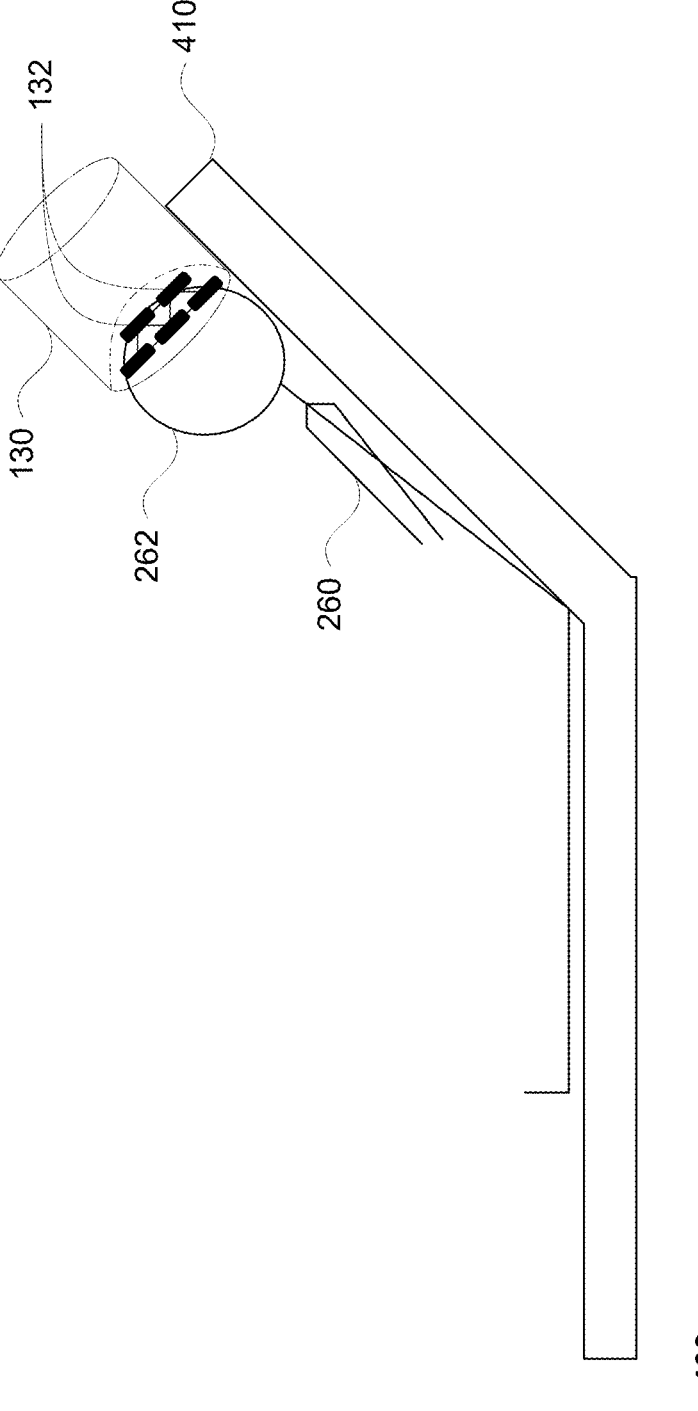
FIG. 4 is an example representation of an individual arranged on a bed or table with a sensor interface in accordance with aspects of the disclosure.

The sensor interface 130 may include a plurality of sensors having quantum properties arranged as one or more quantum sensor arrays. For instance, a quantum sensor array may include Superconducting Quantum Interference Devices (SQUIDs), Optically Pumped Magnetometers (OPM), Optically Pumped Qubit initializers (OPQI), neutral atom gas sensor arrays or potentially other sensors with quantum properties such as those based on Rydberg atoms or trapped ions. As an example, the SQUIDs may include brain magnetic field gradiometers designed to measure the magnetic field gradients generated by brain activity. Such sensors may offer high spatial resolution and sensitivity and may be particularly suitable for detecting even minute changes in a brain's magnetic field. FIG. 4 is an example representation 400 of individual 260 arranged on a bed or table 410. It will be appreciated that such features are not necessarily depicted to scale. In this example, the sensor interface 130 is placed near the head 262 of individual 260. In this configuration, the plurality of sensors (e.g., one or more quantum sensor arrays 132) may measure the magnetic field gradients generated by brain activity of the individual. Although only 5 quantum sensor arrays are depicted, the sensor interface may include any number of sensors depending on the configuration and arrangement of the quantum computing system 100.

The individual sensors of the one or more quantum sensor arrays 132 may be linked in different configurations. In one example, the sensors may be linked internally (sensor to sensor) such that the array is set up as a mesh network (e.g., as represented in the example of FIG. 4) which is linked to the quantum computing apparatus 110 or the classical computing device 120 (e.g. via link 140 or link 142, respectively). Each link may be a classical link or a quantum link. When the sensors are linked quantum mechanically, they may perform rudimentary quantum processing operations before the reduction to classical data is made or this preprocessed quantum data may be provided directly to the computing apparatus. Alternatively, the sensors may be individually linked to the classical computing device or to the quantum computing apparatus. In the process of moving the data between the sensors and computing apparatus it may be converted, or transduced into a different physical media as well as different encoding for the purposes of error correction.

Figure 5:
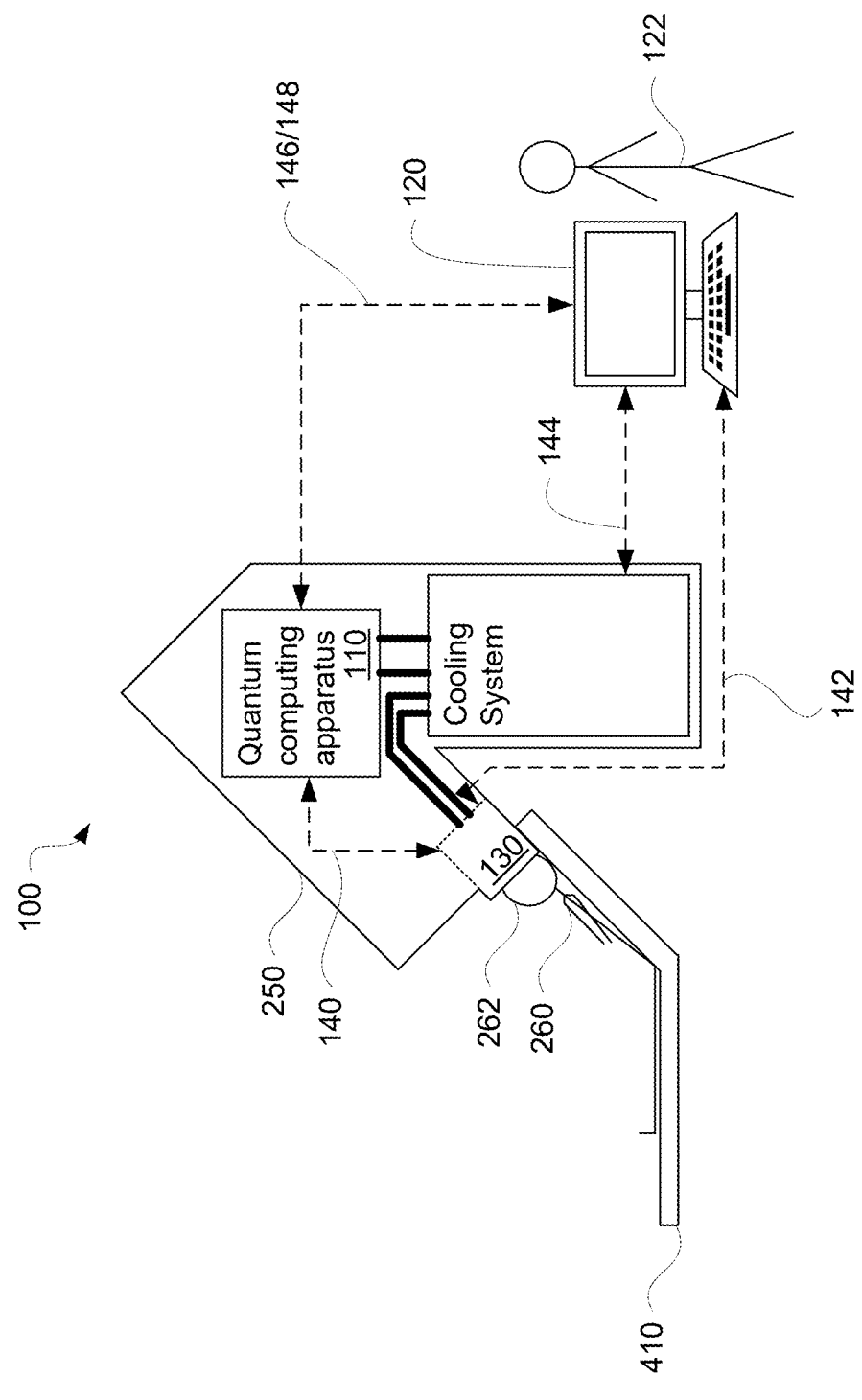
FIG. 5 is an example representation of an individual arranged on a bed or table with a quantum computing system in accordance with aspects of the disclosure.

Depending upon the qubits used, the sensor interface and the quantum computing apparatus 110 may be at least partially and/or fully housed within a super-cooled dewar. FIG. 5 is an example representation 500 of individual 260 arranged on table 410 adjacent to a super-cooled dewar 250. It will be appreciated that such features are not necessarily depicted to scale. The super-cooled dewar 250 may include a cooling system 252 (e.g., a helium dilution refrigerator that uses Helium-3 and/or Helium-4 or other cooling system) which may provide the extremely low temperatures necessary for the operation of the qubits of the quantum computing apparatus 110 as well as those of the one or more quantum sensor arrays 132 of the sensor interface 130. The super-cooled dewar 250 may be designed to maintain a stable, ultra-cold environment to mitigate quantum decoherence and to preserve the qubits' superposition and entanglement states. In some instances, the cooling system may be controlled via a classical computing device, such as the classical computing device 120 via link 144.

Figure 2:
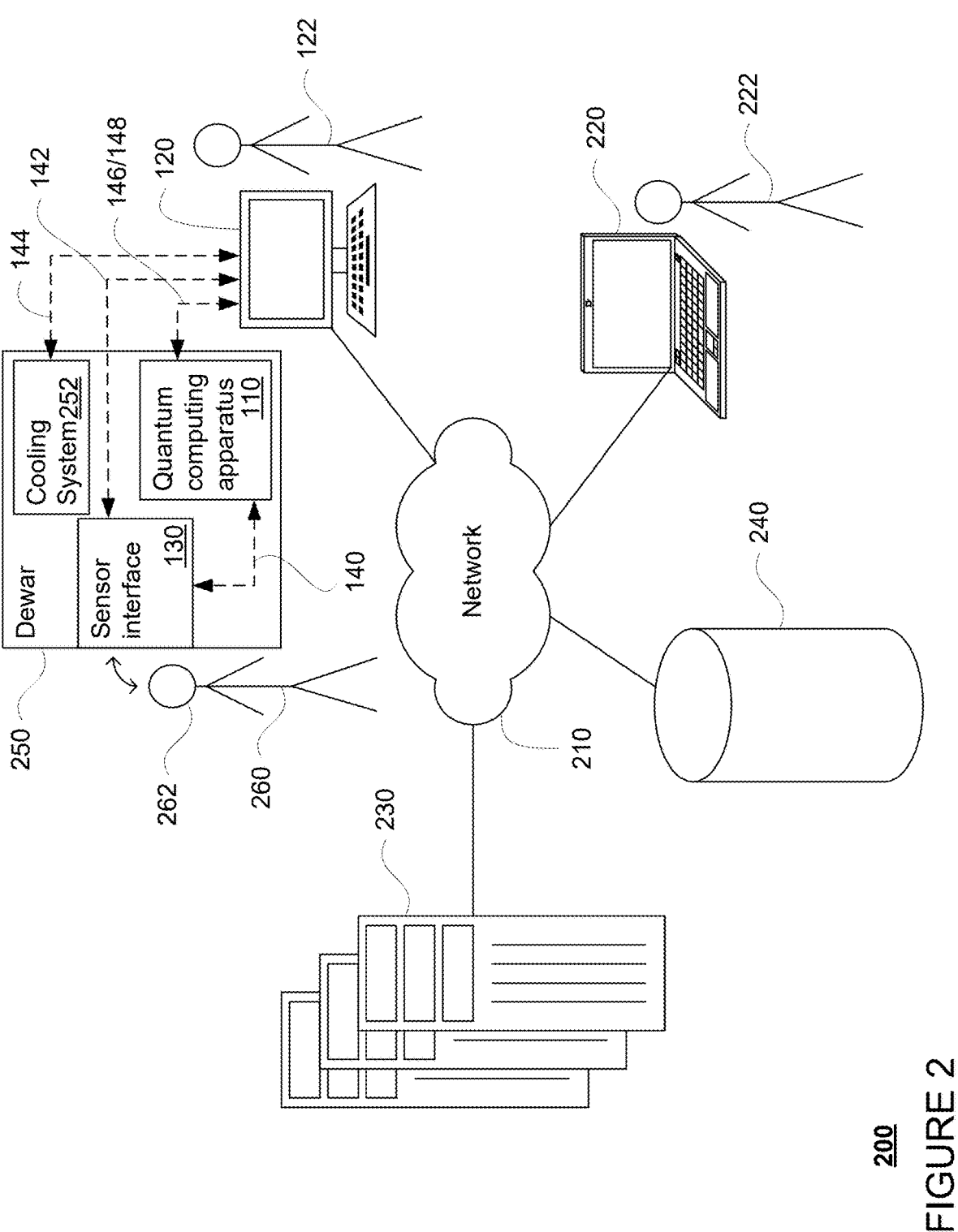
FIG. 2 is an example pictorial diagram of a system in accordance with aspects of the technology.
Figure 3:
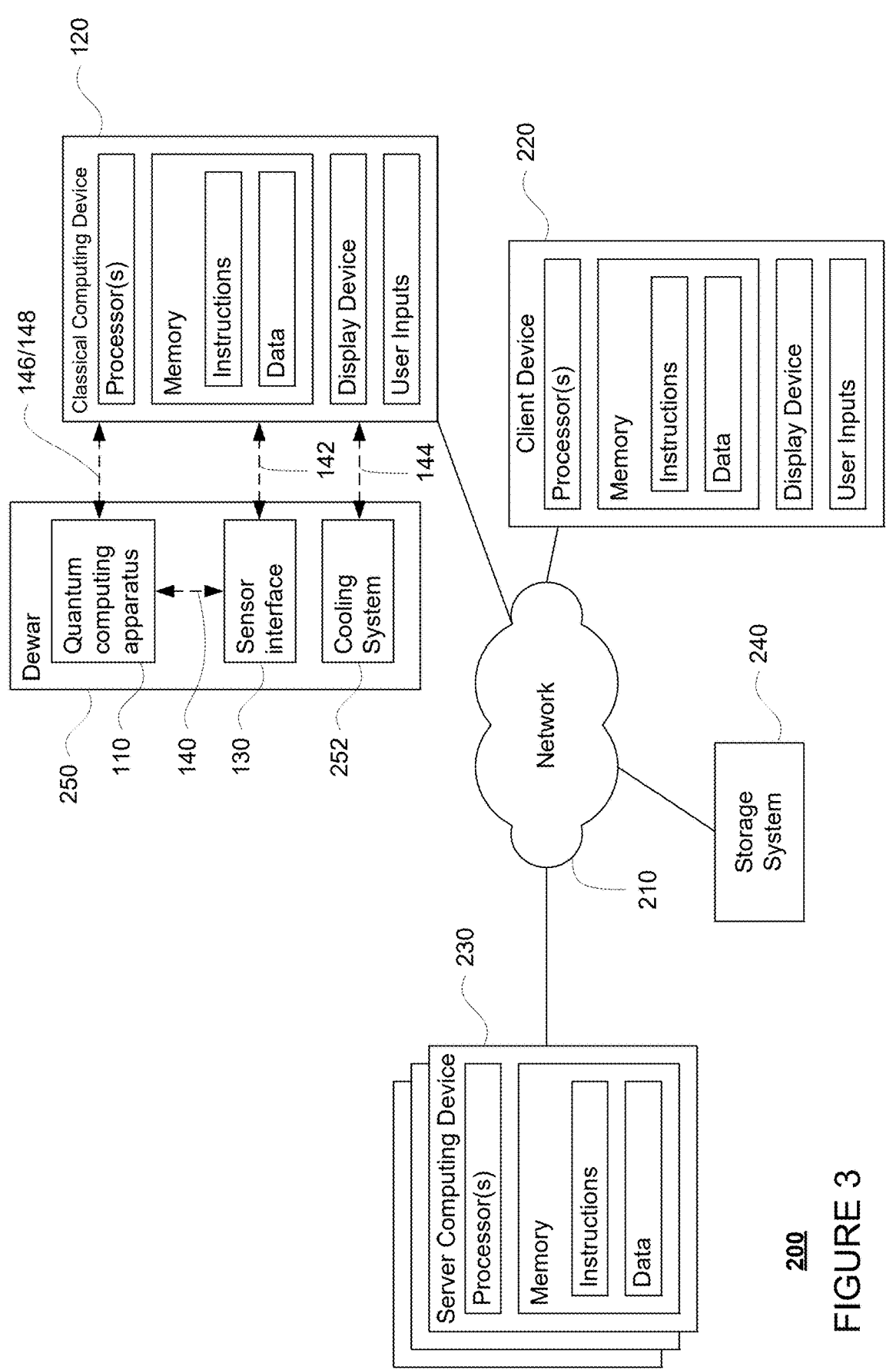
FIG. 3 is an example functional diagram of a system in accordance with aspects of the technology.

As shown in FIGS. 2 and 3, system 200, including the quantum computing apparatus and/or classical computing device may communicate with various other computing devices over a network 210. Such other computing devices may include, for example, client computing device 220 (which may be operated by a user such as user 222), server computing devices 230, and storage system 240.

The network 210, and intervening nodes, may include various configurations and protocols including short range communication protocols such as Bluetooth™, Bluetooth LE™, the Internet, World Wide Web, intranets, virtual private networks, wide area networks, local networks, private networks using communication protocols proprietary to one or more companies, Ethernet, WiFi and HTTP, and various combinations of the foregoing. Such communication may be facilitated by any device capable of transmitting data to and from other computing devices, such as modems and wireless interfaces.

The classical computing device 120, client computing device 220 and server computing devices 230 may include all of the components normally used in connection with a computing device such as the processors and memory described above. The classical computing device and client computing device may also include a user interface subsystem for receiving audio and/or other input from a user and presenting information to the user (e.g., text, imagery, videos and/or other graphical elements). The user interface subsystem may include one or more user inputs (e.g., at least one front (user) facing camera, a mouse, keyboard, touch screen and/or microphone) and one or more display devices (e.g., a monitor having a screen or any other electrical device that is operable to display information (e.g., text, imagery and/or other graphical elements). Other output devices, such as speaker(s) may also provide information to users. In this regard, the client computing device 220 may include one or more of a desktop computer (e.g., as depicted for classical computing device 120) (e.g., a workstation) and a laptop or tablet PC (e.g., as depicted for computing device 220), although other types of client devices may be employed.

In one example, the server computing devices 230 may include a plurality of computing devices, e.g., a load balanced server farm or cloud computing system, that exchange information with different nodes of the network for the purpose of receiving, processing and transmitting the data to and from other computing devices. For instance, the server computing devices 230 may be capable of communicating with any of the classical computing device 120 or client computing device 220 via the network 210.

As with the memory of classical computing device 120, storage system 240 can be of any type of computerized storage capable of storing information accessible by the server computing devices of the system 200, such as a hard-drive, memory card, ROM, RAM, write-capable, and read-only memories. In addition, storage system 240 may include a distributed storage system where data is stored on a plurality of different storage devices which may be physically located at the same or different geographic locations. Storage system 240 may be connected to the computing devices via the network 210 as shown in FIG. 2, and/or may be directly connected to or incorporated into any of the computing devices 120, 220, 230, etc. Storage system 240 may store various types of information, including the historical characterization data discussed further below, which may be retrieved or otherwise accessed by the classical computing device 120, client computing device 220, and/or server computing devices 230, in order to perform all or some of the features described herein.

Systems may include different combinations of the foregoing; whereby different portions of the instructions and data are stored on different types of media. The instructions may be any set of instructions to be executed directly (such as machine code) or indirectly (such as scripts) by the processor(s). For example, the instructions may be stored as computing device code on the computing device-readable medium. In that regard, the terms "instructions", "modules" and "programs" may be used interchangeably herein. The instructions may be stored in object code format for direct processing by the processor, or in any other computing device language including scripts or collections of independent source code modules that are interpreted on demand or compiled in advance.

Example Methods

Figure 9:
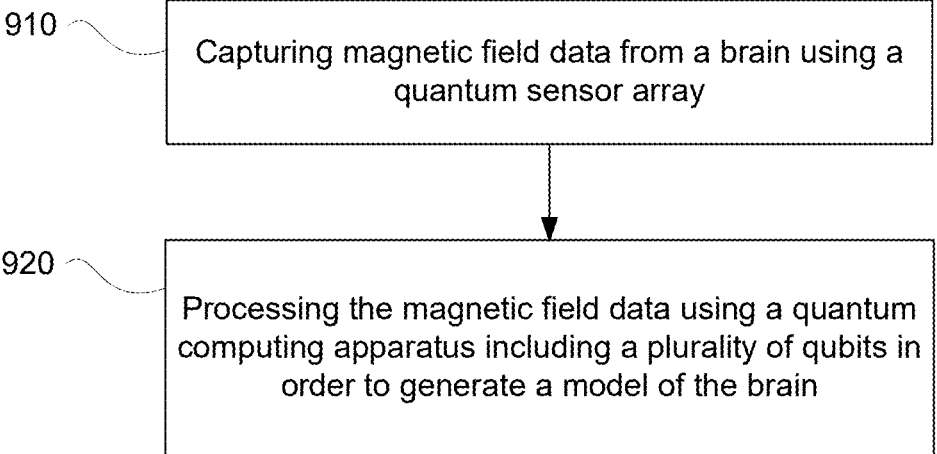
FIG. 9 is an example flow diagram in accordance with aspects of the disclosure.

FIG. 9 depicts an example method 900 for utilizing quantum computing systems for processing of data generated by quantum sensors during magneto-encephalography.

While FIG. 9 shows blocks in a particular order, the order may be varied and multiple operations may be performed simultaneously. Also, operations may be added or omitted.

For instance, at block 910, magnetic field data is captured from a brain using a quantum sensor array. The quantum computing system 100 may be used to collect, process and analyze data generated by the sensors of the sensor interface during a magneto-encephalography test. For example, returning to FIGS. 4 and 5, the one or more quantum sensor arrays 132 of the sensor interface 130 may be placed near the head 262 (or brain) of the individual 260 from which signals are to be collected. In this regard, the sensor interface 130 may include a cap or other device placed on an individual's head, as represented in FIG. 4. Data collection may begin, during which an action may be performed by the individual or some stimulus, such as visual, tactile or audible, may be provided. For example, the individual 260 may be asked to view a video or one or more images or to think of a particular object or feeling. As another example, a seizure may be induced in the individual 260 by providing medications to make the individual drowsy and/or flashing lights. This process may be repeated one or more times, for instance under the same or different conditions, in order to collect additional data.

The individual sensors of the one or more quantum sensor arrays 132 may respond to magnetic fields generated by electrical activity in a brain and generate an output signal representing the gradient of the magnetic field or the rate of change of the magnetic field strength. The magnetic field data may include temporal, spatial, frequency, and phase content. The configuration of the quantum sensor arrays and quantum computing apparatus may potentially also facilitate the collection of signals that may not have otherwise been detectable.

In some instances the signals generated by one or more quantum sensor arrays 132 may be processed minimally within the sensor array via the quantum links. For instance, the quantum sensor array may encode additional data in the output signals. This additional data may include, for example, sensor location and relative phase and timing information internal to the sensor which can be used by a classical computing system or a quantum computing apparatus to process the magnetic field data.

In the future, SQUIDs of the one or more quantum sensor arrays 132 may be capable of collecting and processing coherent real or virtual photons from signals generated by a brain or eye as well as other potential data. In this regard, this data may also be included in the output signals.

Because of the quantum nature of the one or more quantum sensor arrays 132, the output signals may be directly transduced from the sensors to the quantum computing apparatus 110. In this configuration, a resonator may be used as both a field controller for a given qubit as well as an output reader of the qubit's processing of the variables posed to an entangled qubit pair. The output signals may be encoded in a quantum error correcting code, in order to enable further use of the out signals. In some instances, the output signals may be stored in quantum memory of the quantum computing system 100 to for additional processing capacity and to enable the quantum computing system to do additional processing.

Because of the direct connection between the one or more quantum sensor arrays 132, processing can therefore be made in an extremely low noise environment, thereby increasing the signal to noise quality. For example, integrating the quantum computing system 100 inside of super-cooled dewar 250 (as depicted in FIG. 5) may ensure a stable and optimal operating environment for the SQUIDs and the quantum computing apparatus, reducing the risk of errors due to quantum decoherence and other noise sources. The noise reduction may enable faster tests with more reliable results. For instance, fewer output signals may be needed, potentially leading to a "few-shot" or even "single shot" test where one brain electrical event could be interpreted without statistical averaging. This would greatly increase clinical capacity and may potentially capture some events that may only be detected in a single- or few-shot setting.

By integrating one or more quantum sensor arrays 132, the quantum computing apparatus 110, and the classical computing device 120, rapid analysis of timing and simultaneity of brain events during normal and disease brain activities (such as epilepsy) may be accomplished. In addition, this may allow the processors of the quantum computing apparatus 110 to act upon the output signals before measurement or combination with other signals.

Alternatively, the output signals may be processed by the classical computing device 120 or the quantum computing apparatus 110 in order to reduce the output signals to classical field and phase values (e.g. to a phase or amplitude encoded format within a logical error correcting code or "classical data"). These may be stored in classical or quantum memory depending upon the configuration of the quantum computing system 100.

Figure 6:
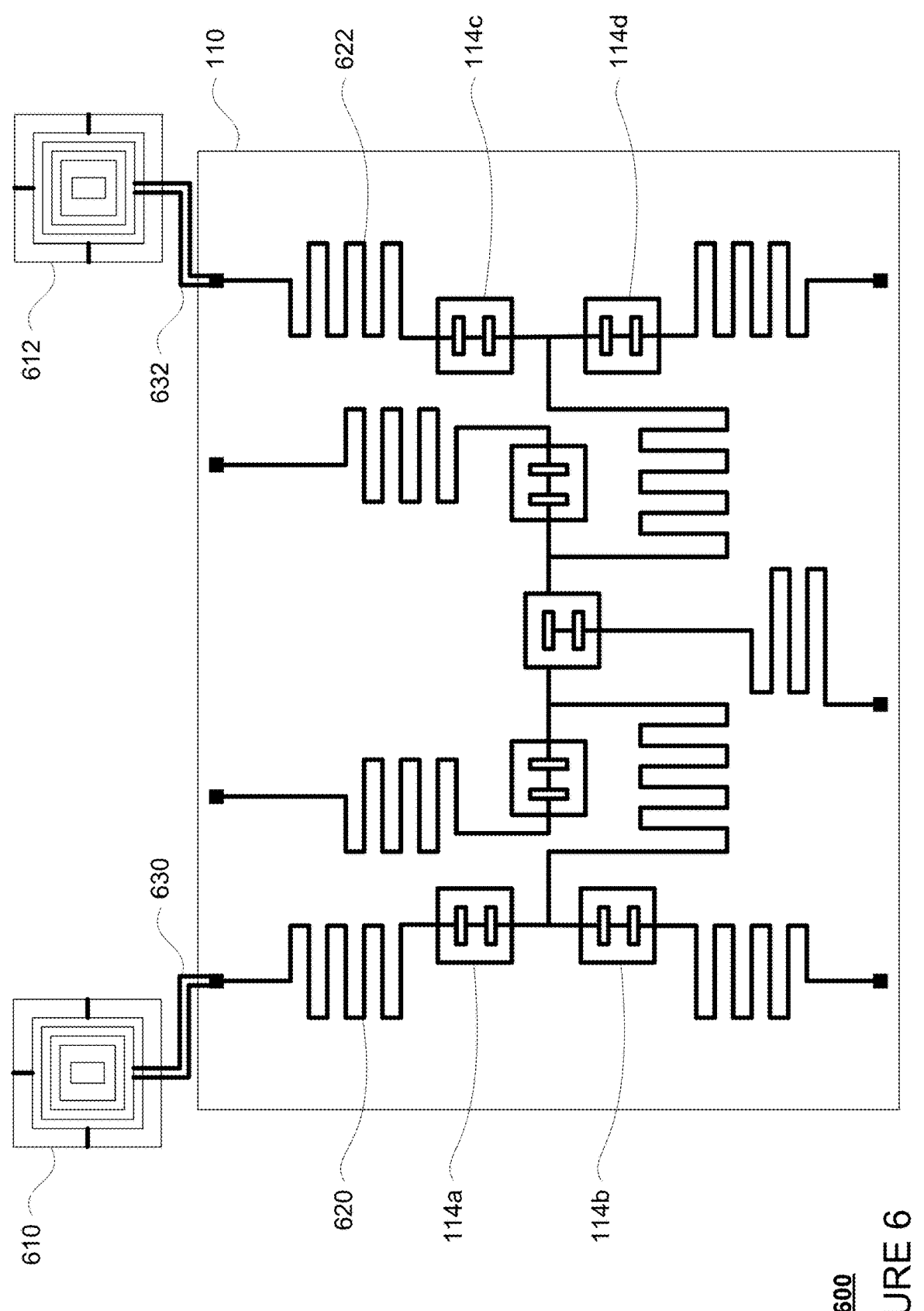
FIG. 6 is an example representation of quantum sensors and aspects of a quantum computing apparatus in accordance with aspects of the disclosure.

FIG. 6 is an example representation 600 of two SQUIDs 610, 612 of the one or more quantum sensor arrays 132 and aspects of the quantum computing apparatus 110. In this example, output signals from the SQUIDs 610, 612 are sent to the quantum computing apparatus 110 directly, for instance via links 630, 632, respectively (corresponding to the link 140). In this regard, the output signals are not first flattened and processed by the classical computing device 120, but remain quantum coherent until the point of eventual measurement. In this example, the output signals from the SQUIDs 610, 612 are fed to resonators 620, 622, respectively, for processing by the qubits 114 (here, qubit 114c and qubit 114c, respectively). As noted above, this may enable the quantum computing apparatus 110 to process the output signals directly. Note that a variety of electronic circuits or other physical devices may be used to modulate the SQUID sensor outputs for appropriate signal conditioning for the Qubit processors. In addition, output signals from previous time points may be kept quantum coherent for any desired length of time.

Returning to FIG. 9, at block 920, the magnetic field data is processed using a quantum computing apparatus including a plurality of qubits in order to generate a model of the brain. The quantum computing apparatus 110 may be used to process the output signals (quantum data) or the classical data. The quantum data may be processed directly with quantum learning algorithms to determine various features of the output signals. In some instances, quantum error correction encodings may be used to preserve and/or purify the output signals as required for processing. This may enable quantum learning algorithms to extract novel signals with exponentially fewer samples in some cases. In this regard, the output signals may be processed in their quantum form rather than after such signals are converted to classical form which may provide significant potential advantages for learning about the individual's brain activity or such activity in general. For instance, processing the output signals in their quantum form by the quantum computing apparatus 110 may enable detection of novel phenomena and mechanisms enabled by primarily quantum pathways.

For the classical data, the encoded data may be used by the quantum computing apparatus 110 with quantum signal processing techniques to extract signals from the data. In this regard, the quantum data or classical data may be run through classical data processing techniques via the quantum computing apparatus 110 or the classical computing device 120. Such techniques may include, for example, such as blind-source separation, frequency analysis, etc. to determine the various features of the output signals. Examples of the various features may include field strength, frequency, phase, source location, and quantum properties such as spatial entanglement, coherence (e.g., energy relaxation times and dephasing time of qubits), contextuality of signal measurements, etc.

In some instances, multiple copies of an output signal, from the same or different ones of the one or more quantum sensor arrays 132, may be captured and processed together before performing a measurement resulting in collapse to a definite state. This may provide benefits such as improved interpretation reliability, speed of analysis, detection of additional information features in instances where the output signals are processed by the quantum computing apparatus or collapsed or processed by a classical computing device.

The quantum computing apparatus 110 may then be used to generate various models. For example, the quantum computing apparatus 110 may generate a model of the physical origin of signal generation within the brain that is fundamentally quantum in nature in that it supports coherence, contextuality, and entanglement. This model may be fit to the various features to better explain the origin of signals within the brain that are collected and analyzed. For example, as an individual, such as individual 260, goes to sleep, normal and/or abnormal origins of brain sleep electrical rhythms, including the 10 Hz Alpha rhythm may be detected. Computed analysis may provide information on the sleep state and quality of that sleep.

As another example, the quantum computing apparatus 110 may generate a model of the underlying signal-action relationship within the individual's brain. This model may be a classical electromagnetic field model (e.g. dipole source) to localize events in space and time using analytic procedures such as an inverse "best fit" describing the signal origin or a novel quantum field model where a coherent photon field models the actions and coordination within the individual's brain. A quantum model here may represent the manifestation of non-classical effects in the emitted field such as entanglement and contextuality. Such effects cannot be accurately represented by a classical dipole source model when considering the full range of quantum measurements that are possible. These models may even be coordinated to brain mechanisms such as vision or abnormal mechanisms like epilepsy depending upon other data about the individual collected during the collection of signals by the one or more quantum sensor arrays.

The models may be used to deliver feedback to the individual in real time (e.g., during the magneto-encephalography test). This feedback may be in the form of additional external stimulus either classical or quantum. In some instances, the entire procedure may be looped to enable control of another device by the individual as discussed further below.

The enhanced computational capacity provided by the quantum computing apparatus 110, which can process the extensive, high-density data produced by the gradiometer sensors in real time may lead to more accurate and detailed models of brain activity, and a deeper understanding of the neural processes underlying cognition and behavior. In addition, the direct linking of the output signal to a quantum processor of the quantum computing apparatus 110 combined with advances in quantum learning algorithms to dramatically improve signal detection. Of course, even the classical data may be processed via a quantum computing apparatus to improve processing times. In other words, either approach may potentially speed the processing of output data that currently bottlenecks processing times resulting from the classical process of capturing magnetic field data in one the system, attempting to convert the data to digital signals for classical computation, exporting these signals through external networks and then managing the output at a completely separate and remote system.

In some implementations, feedback from the quantum computing apparatus 110 may be used to perform different tasks. For example, the magnetic field data generated from across an individual's head, such as head 262 of individual 260, including portions of a brain associated with movement commands may be captured and processed to identify particular actions. These actions may then be used to control another device. Based on the individual's intention, trained and refined through practice, improved signal to noise for control of various devices may be accomplished. For example, overtime such magnetic field data can be processed with additional data (e.g., input from the individual) and used to create a mapping of magnetic field data to particular actions (e.g. a lookup table, database, or deep neural network). The quantum computing apparatus 110, classical computing device 120, and/or another computing device (such as computing device 220) may then send commands to another device which acts upon the particular actions. In this regard, the device may actually be controlled by signals generated by the individual's brain enabling brain/computer interfaces which may be particularly useful for people with disabilities.

In some instances, the signals generated by an individual's brain may be used to directly program and set test variables for quantum computing problems. For instance, with conventional quantum computing variables are programmed to the qubits 114 via the resonator arrays of the readout apparatus 116 which also read out results after collapse. In this regard, in order to control the quantum computing apparatus 110, the output signals may operate as a resonator array for the input qubit variables. The programming of the qubits 114 may be updated or modified by the individual who may be provided with a display of the information of the computation outputs. Such modifications may be enacted by either an external control input (e.g., keyboard, control stick, voice input, etc.) or directly by a brain-machine interface command.

Figure 7:
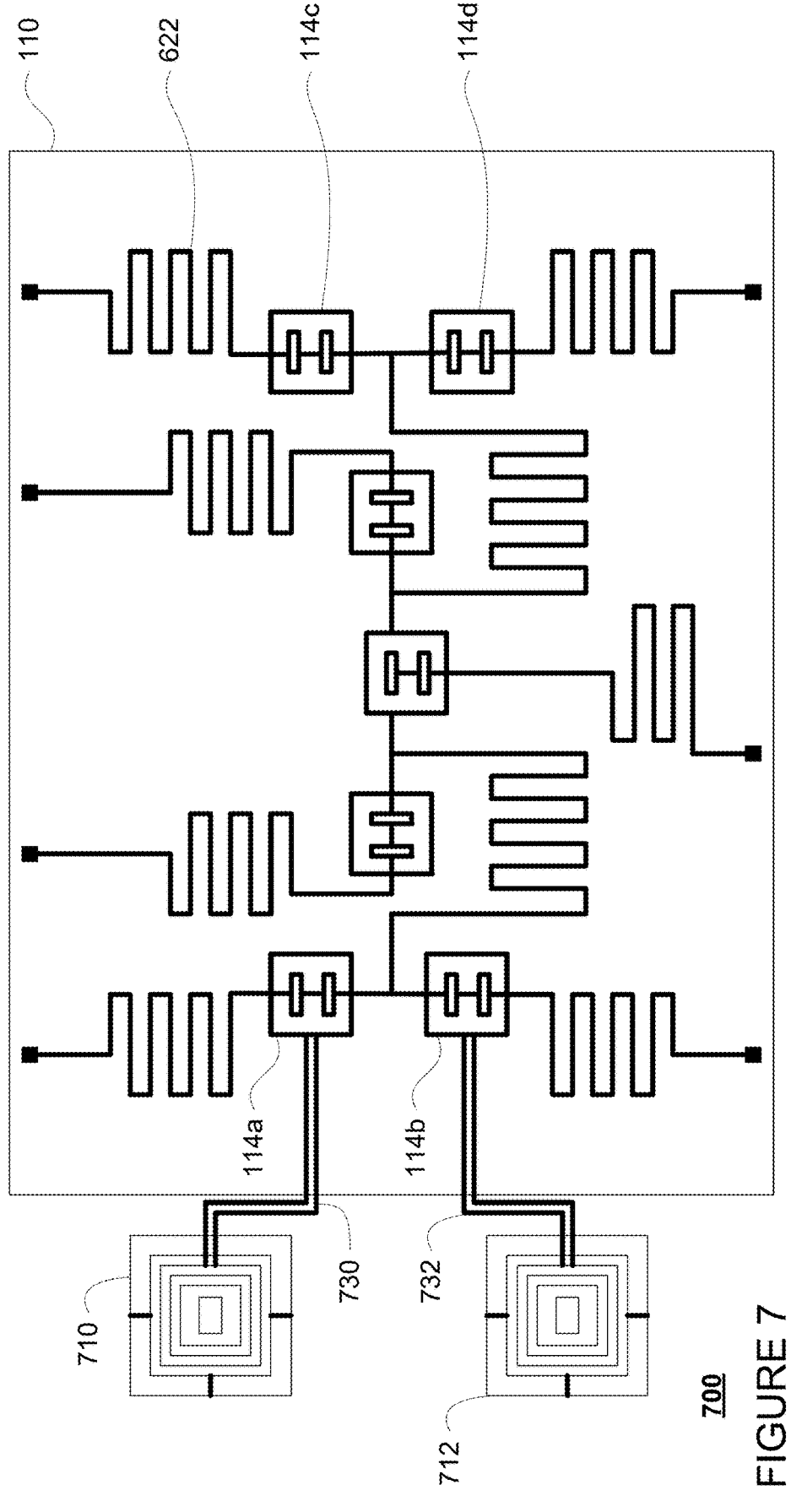
FIG. 7 is an example representation of quantum sensors and aspects of a quantum computing apparatus in accordance with aspects of the disclosure.

FIG. 7 is an example representation 700 of two SQUIDs 710, 712 of the one or more quantum sensor arrays 132 and aspects of the quantum computing apparatus 110. In this example, outputs signals from the SQUIDs 710, 712 are sent to the quantum computing apparatus 110 directly, for instance via links 730, 732, respectively (corresponding to the link 140). In this example, the output signals from the SQUIDs 710, 712 are fed to the qubits 114 (here, qubit 114a and qubit 114b, respectively). In this example, the SQUIDs 710, 712 may function as resonator arrays for input variables to the qubit 114a, 114b.

In some instances, the output of the quantum computing apparatus 110 may be used to improve the signal clarity of the output signals. In other words, feedback from the quantum computing apparatus 110 may be used to adjust or tune the one or more quantum sensor arrays 132, including the SQUIDs themselves. This, in turn, may improve the quality of the output signals. For example, the computed determination of the origin of signals of interest may indicate which quantum sensors in a multi sensor array are most favored for optimum signal detection. Thus the outputs either singly or as a networked out would be modulated in amplitude or other aspects. These modulations would be made by pre-programming of the quantum computing system of the one or more quantum sensor arrays 132 could be adjusted to optimally favor those computed sensor locations and further boost or improve the signal quality. In addition or alternatively, an underlying quantum state of the SQUIDs of one or more quantum sensor arrays may be changed in order to be more sensitive to signals at a particular location and/or increase the sensitivity of some SQUIDs while decreasing the sensitivity of others. This may be achieved, for example, by adjusting the magnitude of magnetic flux applied to the SQUIDs. Of course, the particular details of what is adjusted at a physical level will depend upon the specific architecture of the one or more quantum sensor arrays.

Figure 8:
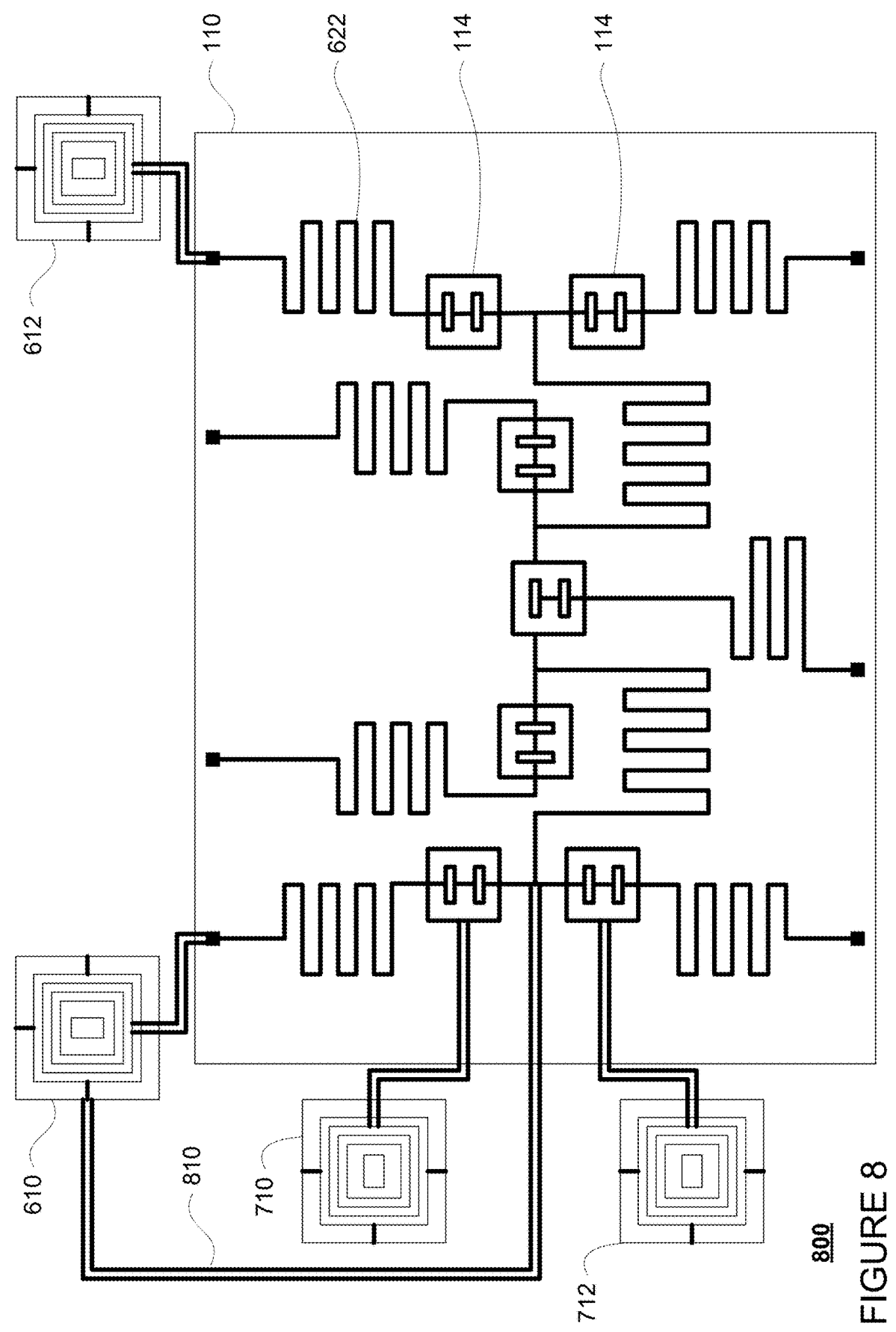
FIG. 8 is an example representation of quantum sensors and aspects of a quantum computing apparatus in accordance with aspects of the disclosure.

FIG. 8 is an example representation 800 of four SQUIDs 610, 612, 710, 712 of the one or more quantum sensor arrays 132 and aspects of the quantum computing apparatus 110. This example combines the features of the example representations 600, 700 and includes an additional feedback loop 810 between the SQUID 610 and qubits 144a, 144b. In a more elaborate set of controls compared to the example 0062 above, the quantum computing outputs can be used to modify the outputs of the MEG sensors for utility purposes. For example, the QC output could be used to stop the MEG output given a particular programmed arrangement.

In error corrected storage of quantum information, the data is preserved by a series of local measurements and updates via a classical decoding algorithm. These algorithms may benefit greatly from dynamically updated models of likely physical errors on the device so as to better identify the most likely sources of corruption and preserve data more effectively with fewer resources. This input from both the local measurements and user input can help with the local qubit management as well as general error correction.

The features described herein may provide a significant improvement over existing technologies, by offering a more sophisticated and powerful tool for data processing and analysis. The features described herein bring the immediate computation power of quantum computing to the problems of clinical and basic neuroscience. In some instances, the output data generated and processed as described herein may reveal different underlying brain activity than classical analysis which may potentially lead to significant advancements in the ability to understand and interact with the brain as well as enable detection of novel phenomena and mechanisms enabled by primarily quantum pathways. This unique combination opens up new possibilities in the fields of quantum sensing and detection, neuroimaging, brain research, diagnostics and diagnosis of diseases of the brain, surgical planning, brain-computer interface systems and more.

Unless otherwise stated, the foregoing alternative examples and embodiments are not mutually exclusive, but may be implemented in various combinations to achieve unique advantages. As these and other variations and combinations of the features discussed above can be utilized without departing from the subject matter defined by the claims, the foregoing description of the embodiments should be taken by way of illustration rather than by way of limitation of the subject matter defined by the claims. In addition, the provision of the aspects described herein, as well as clauses phrased as "such as," "including" and the like, should not be interpreted as limiting the subject matter of the claims to the specific examples or embodiments. Further, the same reference numbers in different drawings can identify the same or similar elements. The processes or other operations may be performed in a different order or simultaneously, unless expressly indicated otherwise herein.

The invention claimed is:

1. A method comprising:
capturing magnetic field data from a brain using a quantum sensor array;
processing the magnetic field data using a quantum computing apparatus including a plurality of qubits in order to adjust a quantum state of the quantum sensor array in order to improve signal quality of the magnetic field data; and
processing the magnetic field data with the improved signal quality using the quantum computing apparatus in order to generate a model of the brain.

2. The method of claim 1, wherein the quantum sensor array includes a plurality of Superconducting Quantum Interference Devices (SQUIDs) configured to measure magnetic field gradients generated by brain activity.

3. The method of claim 2, wherein the adjusting includes adjusting a quantum state of the SQUIDs of one or more of the quantum sensor arrays.

4. The method of claim 2, wherein the adjusting includes increasing the sensitivity of at least one of the plurality of SQUIDs and decreasing the sensitivity of at least one of the plurality of SQUIDs.

5. The method of claim 2, wherein the adjusting includes adjusting a magnitude of magnetic flux applied to the plurality of SQUIDs.

6. The method of claim 1, wherein the quantum sensor array is configured as a mesh network linked to the quantum computing apparatus such that the magnetic field data is processed in quantum form.

7. The method of claim 1, wherein the quantum sensor array and the quantum computing apparatus are each at least partially housed within a dewar.

8. The method of claim 1, further comprising, prior to processing the magnetic field data using the quantum computing apparatus, processing the magnetic field data using a classical computing device including one or more processors to generate classical data such that the classical data is processed by the quantum computing apparatus.

9. The method of claim 1, wherein the model represents physical origin of signal generation within the brain.

10. The method of claim 1, wherein the model is a classical electromagnetic field model.

11. The method of claim 1, wherein the model is a quantum field model where a coherent photon field models actions and coordination within the brain.

12. The method of claim 1, wherein processing the magnetic field data further includes identifying an action, and the method further includes sending a signal to a device in order to cause the device to perform the action.

13. The method of claim 1, wherein the adjusting enables the quantum sensor array to increase sensitivity to signals at a particular location.

14. A system comprising:
a quantum sensor array configured to capture magnetic field data from a brain; and
a quantum computing apparatus including a plurality of qubits and configured to:

process the magnetic field data in order to adjust a quantum state of the quantum sensor array in order to improve signal quality of the magnetic field data; and process the magnetic field data with the improved signal quality using the quantum computing apparatus in order to generate a model of the brain.

15. The system of claim 14, wherein the quantum sensor array is configured as a mesh network linked to the quantum computing apparatus such that the magnetic field data is processed in quantum form.

16. The system of claim 14, wherein the quantum sensor array and the quantum computing apparatus are each at least partially housed within a dewar.

17. The system of claim 14, further comprising a classical computing device including one or more processors configured to, prior to the quantum computing apparatus processing the magnetic field data, process the magnetic field data to generate classical data.

18. The system of claim 14, wherein the model represents physical origin of signal generation within the brain.

19. The system of claim 14, wherein the model is a quantum field model where a coherent photon field models actions and coordination within the brain.

20. The system of claim 14, wherein the quantum computing apparatus is further configured to process the magnetic field data to further identifying an action and to send a signal to a device in order to cause the device to perform the action.

* * * * *